US00PP25984P3

(12) United States Plant Patent
Dirr et al.

(10) Patent No.: US PP25,984 P3
(45) Date of Patent: Oct. 13, 2015

(54) ***DISTYLIUM* PLANT NAMED 'PIIDIST-IV'**

(50) Latin Name: ***Distylium racemosum*×*Distylium myricoides***
Varietal Denomination: PIIDIST-IV

(71) Applicants: Michael A. Dirr, Bogart, GA (US); Joshua H. Kardos, Watkinsville, GA (US)

(72) Inventors: Michael A. Dirr, Bogart, GA (US); Joshua H. Kardos, Watkinsville, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 149 days.

(21) Appl. No.: 13/998,260

(22) Filed: Oct. 16, 2013

(65) Prior Publication Data

US 2015/0106985 P1 Apr. 16, 2015

(51) Int. Cl.
*A01H 5/12* (2006.01)

(52) U.S. Cl.
USPC ..... Plt./226

(58) Field of Classification Search
USPC ..... Plt./226
See application file for complete search history.

*Primary Examiner* — Anne Grunberg
(74) *Attorney, Agent, or Firm* — Lathrop & Gage LLP

(57) ABSTRACT

A new and distinct cultivar of *Distylium* plant named 'PIIDIST-IV', characterized by its compact, upright growth habit, reddish new growth, lustrous, leathery, dark green mature foliage, resistance to insects and disease, and tolerance of wet and dry soil conditions.

2 Drawing Sheets

Genus and species of plant claimed: *Distylium racemosum*×*Distylium myricoides*.

Variety denomination: 'PIIDIST-IV'.

BACKGROUND OF THE INVENTION

The present invention relates to a new and distinct cultivar of *Distylium* plant, botanically known as *Distylium* hybrid, a member of the Hamamelidaceae, and hereinafter referred to by the cultivar name 'PIIDIST-IV'.

'PIIDIST-IV' originated in 2010 as an open-pollinated seedling from seed collected from a *Distylium racemosum* seedling selection (unnamed and unpatented) growing in Watkinsville, Ga. The *Distylium racemosum* was growing in close proximity to several *Distylium myricoides* and *Distylium* hybrid plants. Subsequent DNA analysis of 'PIIDIST-IV' has confirmed its hybrid status between *Distylium racemosum* and *Distylium myricoides*. 'PIIDIST-IV' was selected by the inventor in a cultivated environment in Watkinsville, Ga.

Asexual reproduction of 'PIIDIST-IV' by stem cuttings since 2011 has shown that all the unique features of 'PIIDIST-IV', as herein described, are stable and reproduced true-to-type through successive generations of such asexual propagation.

SUMMARY OF THE INVENTION

Plants of the new cultivar 'PIIDIST-IV' have not been observed under all possible environmental conditions. The phenotype may vary somewhat with changes in light, temperature, soil and rainfall without, however, any variance in genotype.

The following traits have been repeatedly observed and are determined to be unique characteristics of 'PIIDIST-IV'.

These characteristics in combination distinguish 'PIIDIST-IV' as a new and distinct cultivar:

1. Compact, upright growth habit;
3. Reddish new growth;
3. Lustrous, leathery, dark green mature foliage;
4. Resistance to insects and disease; and
5. Tolerance of wet and dry soil conditions.

'PIIDIST-IV' differs from the female parent, *Distylium racemosum*, primarily in growth habit and foliage color. 'PIIDIST-IV' has a smaller, compact, upright growth habit, whereas the female parent has a larger, less compact, upright-spreading growth habit. 'PIIDIST-IV' has darker reddish new growth, whereas the female parent has lighter orange-red new growth.

'PIIDIST-IV' can be compared to 'PIIDIST-IV' (U.S. Plant Pat. No. 24,410), but differs in the following characteristics. 'PIIDIST-IV' has a compact, upright growth habit and reddish new growth, whereas 'PIIDIST-IV' has a less compact, upright-spreading growth habit and yellow-green new growth.

BRIEF DESCRIPTION OF THE DRAWINGS

The accompanying color photographs illustrate the foliage characteristics and the overall appearance of 'PIIDIST-IV', showing the colors as true as it is reasonably possible to obtain in color reproductions of this type. Colors in the photographs may differ slightly from the color values cited in the detailed botanical description which accurately describe the colors of 'PIIDIST-IV'.

DETAILED DESCRIPTION

Figure 1:
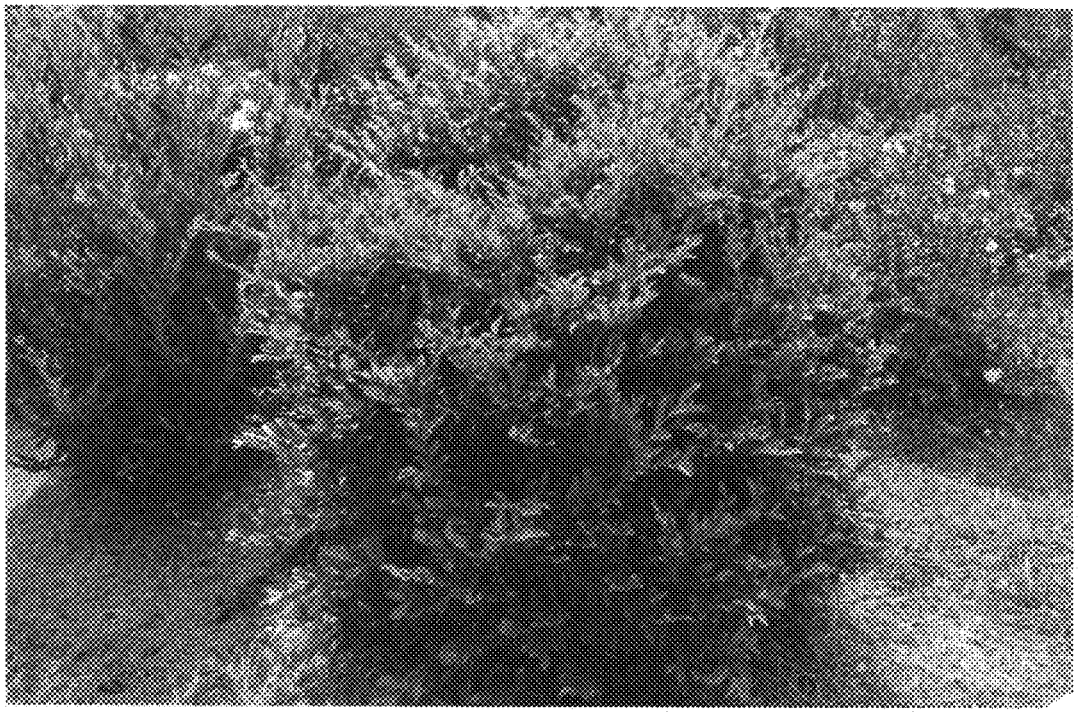
FIG. 1 illustrates the overall appearance and growth habit of 'PIIDIST-IV'.
Figure 2:
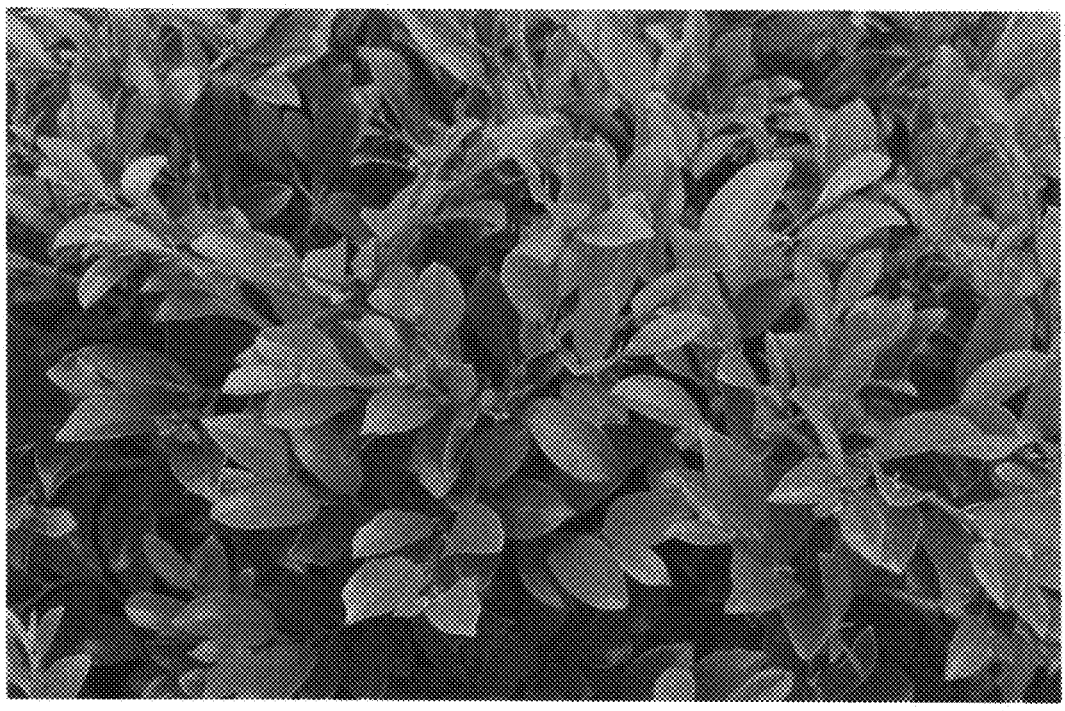
FIG. 2 illustrates a close-up view of the new growth and mature foliage of 'PIIDIST-IV'.

In the following description, color references are made to The Royal Horticultural Society Colour Chart, 2007 Edition, except where general terms of ordinary dictionary significance are used. The plant used for the description was approximately 4-years-old and was grown in the ground in Watkinsville, Ga.

Botanical classification: *Distylium* hybrid 'PIIDIST-IV'. Parentage: female parent: *Distylium racemosum* seedling selection (unnamed and unpatented), male parent: unknown (open-pollinated). Propagation: stem cuttings. Time to initiate roots in summer: about 5 weeks at 32° C.

Plant description: Broadleaf, evergreen, flowering shrub; multi-stemmed; compact, upright growth habit. Freely branching; removal of the terminal bud enhances lateral branch development.

*Root description.*—Medium, well-branched.

*Plant size.*—The original plant, now about four-years-old in the ground, is about 170 cm high from the soil level to the top of the foliage and about 145 cm wide.

*First year stems.*—Having a diameter of about 2.5 mm. Shape: round. Fine pubescence on young stems, becoming glabrous with maturity. Approximately 10 lenticels per 1 cm of stem length. Lenticels are about 0.5 mm in diameter and N199B in color.

*First year stem color.*—176B on new growth, changing to 146C, and finally maturing to 199A.

*Second year and older stems.*—Have a diameter of about 4 mm or more. Shape: round.

*Second year and older stem color.*—199A.

*Stem strength.*—Flexible when young, less flexible once mature.

*Internode length.*—About 1.8 cm.

*Trunk diameter.*—About 5.7 cm at the soil line. Color: N199A. Bark does not exfoliate, covered with lenticels about 1 mm in diameter and N199B in color. Approximately 25 lenticels per 1 cm of stem length.

Vegetative bud description:

*Arrangement.*—Alternate.

*Shape.*—Ovoid with fused, finely pubescent bud scales.

*Size.*—About 4 mm in length and about 2 mm in width.

*Color.*—199A.

Foliage description:

*Arrangement.*—Alternate, simple.

*Length.*—About 5.7 cm.

*Width.*—About 2.3 cm.

*Shape.*—Narrow-oblong to obovate.

*Apex.*—Obtuse.

*Base.*—Broadly tapering to rounded.

*Margin.*—Entire, often undulate.

*Texture* (*upper and lower surfaces*).—Lustrous, thick, leathery.

*Venation pattern.*—Pinnate.

*Venation color* (*upper surface*).—Midrib color is 146C and secondary vein color is 147A.

*Venation color* (*lower surface*).—Midrib color is N144D and secondary vein color is N137B.

*Color of emerging foliage* (*upper surface*).—183A.

*Color of emerging foliage* (*lower surface*).—147C.

*Color of mature foliage* (*upper surface*).—147A.

*Color of mature foliage* (*lower surface*).—146B.

*Petiole length.*—About 5 mm.

*Petiole diameter.*—About 1.5 mm.

*Petiole color* (*upper and lower surfaces*).—146B. Finely pubescent.

Flower description: The original plant, now four-years-old, has not flowered to date.

Fruit: The original plant, now four-years-old, has not produced fruit to date.

Disease/pest resistance: Plants of the new *Distylium* grown in the nursery and garden have exhibited resistance to pathogens and pests common in these environments. 'PIIDIST-IV' is cold hardy in USDA Hardiness Zones 7-9.

We claim:

1. A new and distinct *Distylium* plant named 'PIIDIST-IV', as illustrated and described herein.

* * * * *